US012741919B2

(12) United States Patent
Gerasymchuk et al.

(10) Patent No.: US 12,741,919 B2
(45) Date of Patent: Sep. 22, 2026

(54) METHOD AND DEVICE FOR THE PHOTOINDUCED CONVERSION OF CO2 TO METHANOL

(71) Applicant: INSTYTUT NISKICH TEMPERATUR I BADAN STRUKTURALNYCH PAN IM.W.TRZEBIATOWSKIEGO, Wroclaw (PL)

(72) Inventors: Yuriy Gerasymchuk, Swieta Katarzyna (PL); Pawel Gluchowski, Wroclaw (PL); Wlodzimierz Mista, Wroclaw (PL); Wieslaw Strek, Bielany Wroclawskie (PL); Przemyslaw Wiewiorski, Wroclaw (PL); Robert Tomala, Wroclaw (PL)

(73) Assignee: INSTYTUT NISKICH TEMPERATUR I BADAN STRUKTURALNYCH PAN IM.W.TRZEBIATOWSKIEGO, Wroclaw (PL)

( * ) Notice: Subject to any disclaimer, the term of this patent is extended or adjusted under 35 U.S.C. 154(b) by 579 days.

(21) Appl. No.: 18/255,011

(22) PCT Filed: Nov. 29, 2021

(86) PCT No.: PCT/PL2021/050083
§ 371 (c)(1),
(2) Date: May 30, 2023

(87) PCT Pub. No.: WO2022/119463
PCT Pub. Date: Jun. 9, 2022

(65) Prior Publication Data

US 2024/0002318 A1 Jan. 4, 2024

(30) Foreign Application Priority Data

Dec. 2, 2020 (PL) ........................................ 436198

(51) Int. Cl.

| | |
|---|---|
| ***C07C 29/159*** | (2006.01) |
| ***B01J 8/00*** | (2006.01) |
| ***B01J 21/18*** | (2006.01) |
| ***B01J 35/39*** | (2024.01) |

(52) U.S. Cl.
CPC ............ *C07C 29/159* (2013.01); *B01J 8/008* (2013.01); *B01J 21/18* (2013.01); *B01J 35/39* (2024.01)

(58) Field of Classification Search
CPC . B01J 19/123; B01J 21/18; B01J 35/39; B01J 8/008; C07C 29/159; C07C 31/04
See application file for complete search history.

(56) References Cited

FOREIGN PATENT DOCUMENTS

| | | | | |
|---|---|---|---|---|
| CN | 105289421 | * | 2/2016 | ................ B01J 8/02 |
| CN | 205146185 U | | 4/2016 | |
| CN | 105289421 B | | 9/2017 | |
| PL | 208030 B1 | | 9/2008 | |

OTHER PUBLICATIONS

International Publication (WO2022/119463) with International Search Report (PCT/PL2021/050083).
Adekoya David et al., "Recent trends in photocatalytic materials for reduction of carbon dioxide to methanol", Renewable and Sustainable Energy Reviews, vol. 116, Dec. 1, 2019 (Dec. 1, 2019), p. 109389, XP055896715.
Hsin-Cheng Hsu et al. "Graphene oxide as a promising photocatalyst for CO2 to methanol conversion", Nanoscale, 2013, 5, 262.
Xiaoqiang An et al. "Cu2O/Reduced Graphene Oxide Composites for the Photocatalytic Conversion of CO2", Chemsuschem, 2014, 7, 1086.
Nazimek Dobieslaw and Bozena Czech "Artificial photosynthesis—CO2 towards methanol", Materials Science and Engineering 2011, 19, 012010.
Ganesh Ibram, "Conversion of Carbon Dioxide to Methanol Using Solar Energy", Current Science, 2011, 6, 101, 731.

* cited by examiner

*Primary Examiner* — Pancham Bakshi
(74) *Attorney, Agent, or Firm* — Taro Yaguchi

(57) ABSTRACT

The invention relates to a method for producing methanol by the $CO_2$ conversion route in a photocatalytic process, wherein a base liquid (A) in the form of demineralized and $CO_2$-saturated water is provided to the reaction tank (1) and graphene material (B) is provided and the contents of the reaction tank (1) is exposed to electromagnetic radiation with a wavelength in the UV-VIS-FIR range that is generated by an emitter (D). The invention also relates to an installation for implementing the method.

2 Claims, 1 Drawing Sheet

METHOD AND DEVICE FOR THE PHOTOINDUCED CONVERSION OF CO2 TO METHANOL

FIELD OF THE INVENTION

The present invention relates to a method and device for the photoinduced conversion of $CO_2$ to methanol.

BACKGROUND OF THE INVENTION

Methods of $CH_3OH$ synthesis by the photocatalytic reaction of $CO_2$ dissolved in water using nanoscale catalysts are known [I. Ganesh, Conversion of carbon dioxide to methanol using solar Energy, Current Science 101, 731, 2011].

Methods of photostimulated $CH_3OH$ synthesis using water-dispersed graphene oxide particles as catalysts are also known [Hsi-Cheng Hsu et al., Graphene oxide as promising photocatalyst for $CO_2$ to methanol conversion, Nanoscale 5, 262, 2013; Xiaogiang An et al. $Cu_2O$/Reduced Graphene Oxide Composites for the Photocatalytic Conversion of $CO_2$, ChemSusChem 7, 1086, 2014].

Methods for producing methanol by a photocatalytic method using Ru and $WO_3$-modified $TiO_2$ are also known in the art [D. Nazimek, B. Czech, Mat. Sci. Eng. 19, 012010, 2011; patent PL208030B1].

In the course of research and development work, the Inventors developed a new method of methanol synthesis by photoinduced $CO_2$ conversion.

SUMMARY OF THE INVENTION

The subject of the invention is a method for producing methanol by the $CO_2$ conversion route in a photocatalytic process, wherein a base liquid (A) in the form of demineralized and $CO_2$-saturated water is provided to the reaction tank (1) and graphene material (B) is provided, then the contents of the reaction tank (1) is exposed to electromagnetic radiation with a wavelength in the UV-VIS-FIR light wave range that is generated by an emitter (D).

According to the method of the invention, bringing the electromagnetic radiation beam to the reaction mixture in the tank (1) by means of the emitter (D) results in the formation of the photoelectric effect, i.e. the release of free electrons $e^-$ from graphene material (B), followed, as a result, by a cascade of chemical reactions:

first, ionization of water in the base liquid (A) according to the reaction equation:

$$H_2O \rightarrow 2H^+ + 2e^- + \frac{1}{2}O_2 \quad (1)$$

and then reduction of the carbon dioxide contained in the base liquid (A) to methanol according to the reaction equation:

$$CO_2 + 6H^+ + 6e^- \rightarrow CH_3OH + H_2O \quad (2).$$

Preferably, the method of the present invention uses water in a critical or sub-critical state that allows high $CO_2$ saturation, wherein the $CO_2$ concentration in the base liquid is 7 g/l.

In the method according to the invention, the reaction catalyst is the graphene material (B) which can be provided to the reaction tank (1) in the form of particles, graphene oxide, graphene foam, wherein the graphene material (B) in such a form is dispersed in the base liquid (A). In addition, as a result of the release of gases during the process, graphene material (B) particles are picked up and evenly suspended in the entire volume of the base liquid (A) to form a suspension. In the method according to the invention, an aerogel block can also be used as graphene material (B), which is placed in the reaction tank (1).

Preferably, the method according to the invention uses graphene material (B) wherein the graphene particle size is from 0.1 to 100 μm, wherein the graphene material (B) is in the form of graphene oxide powder, porous graphene, graphene flakes, an aerogel or graphene dots of sizes from 0.1 to 100 μm.

Preferably, the concentration of the graphene material (B) in the reaction tank (1) is 0.1 μg per 1 g of demineralized water (without $CO_2$).

The method according to the invention may also be implemented using the base liquid (A) with the addition of other optically inactive substances for which the moment of methanol separation enables the initiation of a chemical process (e.g. gelling).

In the method according to the invention, the emitter (D) operates in a continuous or pulsed mode, emitting electromagnetic waves with a wavelength in the range of 400-1100 nm, preferably 650-1100 nm.

The method according to the invention can be implemented in a continuous or periodic mode in tanks with a specified amount of substrates and tanks with a constant supply of raw materials (base liquid A) and graphene material (B) and with the methanol receipt, such as photodistillators.

According to the invention, the method is conducted in the reaction tank (1), wherein at least a part of the surface must be made of a transparent material partially or completely transmittable for the UV-VIS-FIR light wave range, for example, it can be a closed capsule, can or reactor with a window transparent for electromagnetic radiation. In the case when only a part of the tank surface is transmittable for the UV-VIS-FIR light waves, such a window is located at the bottom of the reaction tank (1), because then, under the tank, there is an optical system emitting electromagnetic radiation. A schematic diagram of conducting the method according to the invention is shown in FIG. 1.

Also the subject of the present invention is an installation for the production of methanol by the $CO_2$ conversion route in a photocatalytic process, equipped with a reaction tank (1) made of a transparent material partially or completely transmittable for the UV-VIS-FIR light wave range, connected from the top to a base liquid tank (9) provided with a programmable injection pump and connected from the top to a vapour condenser subsystem (13), wherein the vapour condenser subsystem (13) is connected in the upper part to a deaerator (14) and in the lower part to an intermediate tank (13) for methanol, and further the intermediate tank (13) through a valve (16) is connected to the target tank (17) for methanol equipped with a programmable pump, the reaction tank (1) further contains a graphene suspension (2) and the reaction tank (1) is connected from the top by a carrier gas supply (10) to a process controller (11) connected to the carrier gas installation (12), in the part where the reaction tank (1) is made of transparent material partially or completely transmittable for the UV-VIS-FIR light wave range, there is an optical system (8) equipped with a light sensor (F) and connected by an optical fiber (7) to an electromagnetic radiation emitter (6), wherein the reaction tank (1) is embedded in the body (3) by means of a mounting (4) and additionally in the lower part of the reaction tank (1) there is a temperature sensor (T), and in the upper part of the reaction tank (1) there is a pressure sensor (P).

According to the invention, the light emitter (6, D) can be a LED power matrix (6A) or a halogen lamp with a reflector (6B) and luminescent diodes, laser diodes or lasers. When using a graphene block as an aerogel catalyst, it is preferable to use a focused laser radiation beam emitting white light as the emitter (D).

BRIEF DESCRIPTION OF THE DRAWINGS

The solution according to the invention is illustrated in the drawings, in which.

DETAILED DESCRIPTION OF THE INVENTION

Description of Embodiments

The present invention is presented in more detail in an embodiment, which does not limit the scope thereof.

EXAMPLES

Example 1

Methanol Capsule with a Programmed Concentration Thereof

Figure 1:
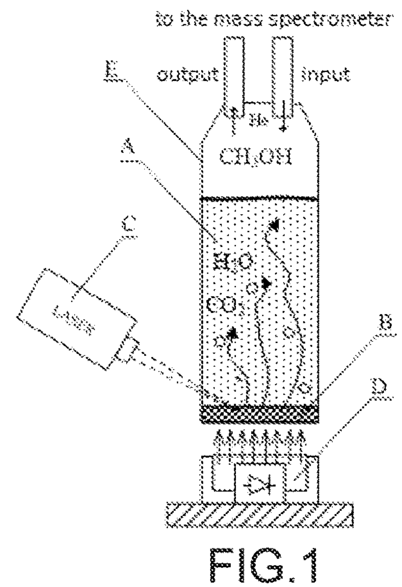
FIG. 1 shows a schematic diagram of producing methanol by the method according to the invention using capsule A—base liquid ($H_2O+CO_2$), B—graphene (flakes, aerogel), C—laser, D—LED, E—body (capsule, can, reactor) with a transparent window(-s) made of quartz (glass)

A small amount of graphene B (0.1 μg/1 g water) in the form of fine flakes, foams or an aerogel is placed in a transparent capsule (or with a quartz window) containing $CO_2$-saturated water as the base liquid A. Operating the light beam from the laser C or led D source (or mixed) causes the generation of methanol to a specific concentration thereof (from 1% to 18%) in water. Concentration programming is done by a suitable time of exposure to light or by the luminous flux intensity. The capsule can then be subjected to a standard distillation process in order to obtain methanol. A schematic diagram of the implementation of the method according to the invention using a capsule is shown in FIG. 1.

The solution can be used in photocatalytic hydrogen generators based on photolysis, wherein preferred methanol concentrations are up to 2%.

Example 2

Methanol Photodistillator Using Graphene as a Catalyst

Figure 2:
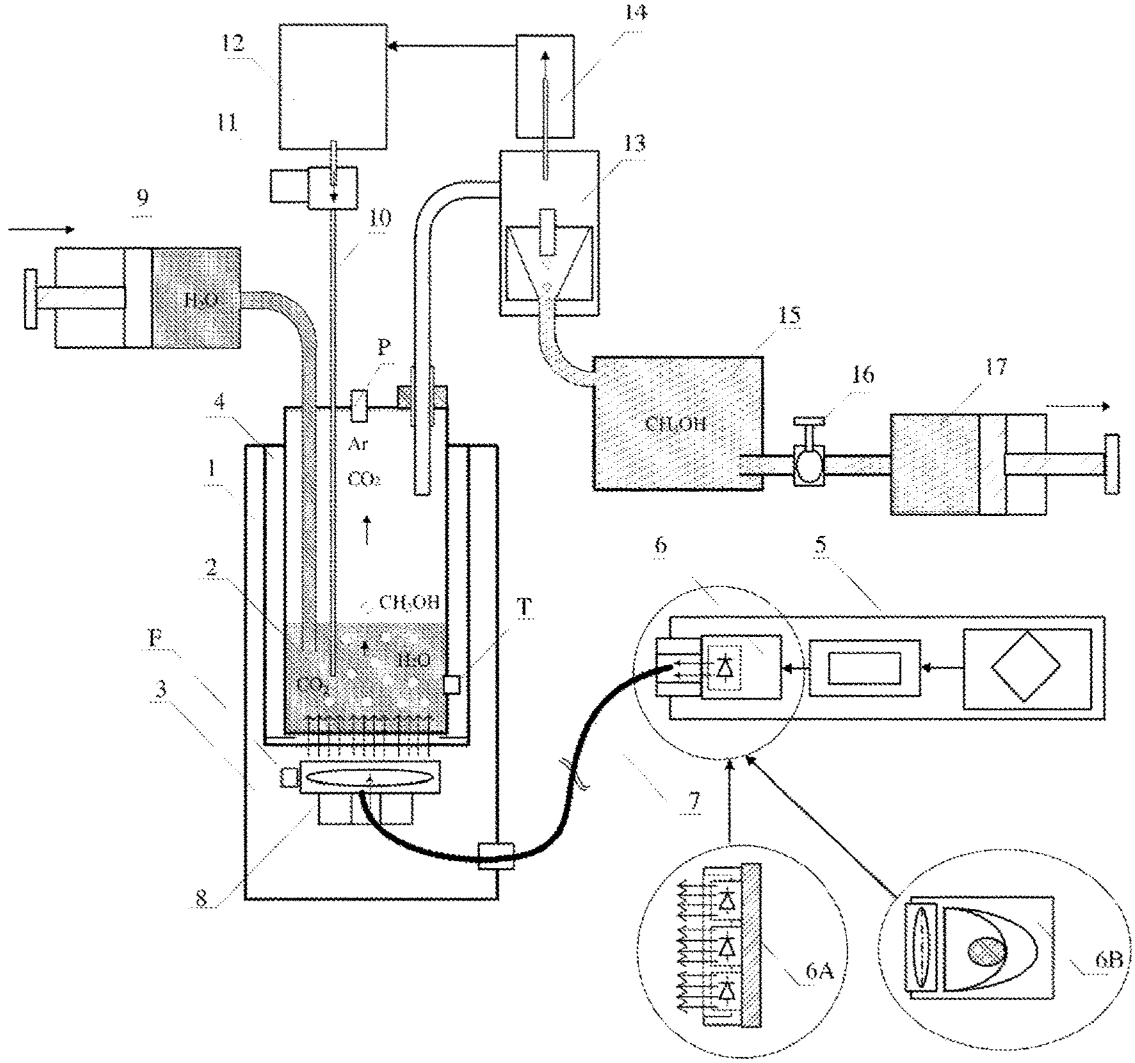
FIG. 2 shows a vertical cross-section of the device for producing methanol in a production cycle (photodistillator), a list of designations: 1—photocatalytic reactor (chemical reactor subsystem), 2—graphene suspension in highly $CO_2$-saturated water, 3—body of the catalytic reactor, 4—mounting of the photoreactor (of transparent quartz, or with a quartz window), 5—illuminator subsystem (laser, LED, halogen), 6—light emitter: laser diode, 6A—LED power matrix, 6B—halogen lamp with a reflector, 7—optical fiber, 8—optical system, 9—water tank with a programmable injection pump, 10—carrier gas (Ar, $CO_2$) supply, 11—process controller (mass flow controller, pressure controller), 12—carrier gas installation, 13—vapor condenser subsystem with a purifier (distillator), 14—deaerator, 15—intermediate tank for methanol, 16—programmable valve, 17—target tank for methanol with a programmable pump, T—temperature sensor, F—light sensor.

FIG. 2 shows a diagram of a device for producing methanol in a photocatalytic process. Suspension based on demineralized water subjected to $CO_2$ saturation, wherein particles of flaky graphene are present, was placed in a transparent photocatalytic reactor 1. In suspension 2, graphene should preferably be as fragmented as possible (micrometric graphene particle size, most preferably graphene dots). The entire reactor is placed in a stable and thermally insulated body as a chemical reactor 3. The photocatalytic reactor 1 is most preferably arranged in the body 3 so as to obtain the smallest possible optical and thermal losses due to the mounting 4 system provided. Suspension 2 is exposed to the beam of light from the irradiation system 5 based on laser devices 6 (semiconductors, or Nd:YAG). The irradiator 5 system may be based on high-power LEDs 6A (LED/laser matrix) or halogen lighting (HID) 6B. The suspension can be irradiated from anywhere (from the bottom, from the side, from the top) depending on the target detailed design of the device. Using the optical fiber beam 7 connected to a dedicated optical system 8 (lens system) is preferred. Preferably, the water quantity level (suspension concentration) is replenished by a programmable pump 9 integrated with the tank. Oxygen is pushed out of the photoreactor through the carrier gas system 10 (Argon, $CO_2$) from the gas installation 11. Methanol vapours generated in the photocatalytic process together with other gas products pass to the selective methanol condenser 13 with a degassing system 14. Methanol condensates are collected in the intermediate tank 15. Liquid methanol is received through a programmable valve 16 into a target tank 17 equipped with a pump.

Based on the above solution with an adapted fuel cell, it is possible to implement an electric current generator based on a PEM fuel cell powered from the methanol generated in the photocatalytic process by irradiating the suspension of $CO_2$-saturated water and graphene.

What is claimed is:

1. An installation for the production of methanol by the $CO_2$ conversion route in a photocatalytic process, equipped with a reaction tank (1) made of a transparent material partially or completely transmittable for the UV-VIS-FIR wavelength, connected from the top to a base liquid tank (9) provided with a programmable injection pump and connected from the top to a vapour condenser subsystem (13), wherein the vapour condenser subsystem (13) is connected in the upper part to a deaerator (14) and in the lower part to an intermediate tank (13) for methanol, and further the intermediate tank (13) through a valve (16) is connected to the target tank (17) for methanol equipped with a programmable pump, the reaction tank (1) further contains a graphene suspension (2) and the reaction tank (1) is connected from the top by a carrier gas supply (10) to a process controller (11) connected to the carrier gas installation (12), in the part where the reaction tank (1) is made of transparent material partially or completely transmittable for the UV-VIS-FIR wavelengths, there is an optical system (8) equipped with a light sensor (F) and connected by an optical fiber (7) to an electromagnetic radiation emitter (6), wherein the reaction tank (1) is embedded in the body (3) by means of a mounting (4) and additionally in the lower part of the reaction tank (1) there is a temperature sensor (T), and in the upper part of the reaction tank (1) there is a pressure sensor (P).

2. The installation according to claim 1, characterized in that the electromagnetic radiation emitter (6) can be a LED power matrix (6A) or a halogen lamp with a reflector (6B).

* * * * *